United States Patent

Hokama et al.

(10) Patent No.: US 6,770,490 B1
(45) Date of Patent: Aug. 3, 2004

(54) MEMBRANE IMMUNOBEAD ASSAY FOR THE DETECTION OF CIGUATOXIN AND RELATED POLYETHER MARINE TOXINS

(75) Inventors: Yoshitsugi Hokama, Honolulu, HI (US); Joanne S. M. Ebesu, Honolulu, HI (US); Warren E. Takenaka, Honolulu, HI (US); Robert E. Bourke, Honolulu, HI (US); Patrick K. Sullivan, Honolulu, HI (US)

(73) Assignee: Oceanit Test Systems, Inc., Honolulu, HI (US)

( * ) Notice: Subject to any disclaimer, the term of this patent is extended or adjusted under 35 U.S.C. 154(b) by 788 days.

(21) Appl. No.: 09/115,797

(22) Filed: Jul. 15, 1998

(51) Int. Cl.$^7$ .................... G01N 33/53; G01N 33/567; G01N 21/00; G01N 31/22; G01N 31/00

(52) U.S. Cl. .................... 436/808; 435/7.1; 435/7.2; 435/40.5; 436/164; 436/168; 436/177; 436/538; 436/541; 436/805; 436/807; 436/808; 436/823; 436/824; 436/20

(58) Field of Search .................... D10/81; 435/7, 435/7.1, 7.21; 436/805, 808, 807, 823, 49, 20, 538, 541, 164, 168, 177, 824; 422/56, 61

(56) References Cited

U.S. PATENT DOCUMENTS

| | | | | |
|---|---|---|---|---|
| 4,816,392 A | * | 3/1989 | Hokama | 435/7 |
| 5,206,141 A | * | 4/1993 | Park | 435/7.1 |
| 5,238,652 A | | 8/1993 | Sun et al. | |
| 5,266,497 A | | 11/1993 | Imai et al. | |
| 5,286,498 A | | 2/1994 | Park et al. | |
| 5,525,525 A | * | 6/1996 | Hokama | 436/523 |

OTHER PUBLICATIONS

Hokama et al. 1983. Toxicon. 21(6): 817–824.*
Hokama. 1985. Toxicon. 23(6):939–946.*
Hokama et al. 1988. Lecture Notes on Costal and Estuarine Studies. 25:155–165.*
Hokama. 1990. J. of Clin. Lab. Ana. 4:213–217.*
Bangs, L.B., "Latex Agglutination Tests", Amer. Clinical Lab. News Edition, Jun. 1988, pp. 20–25.
Bangs, L.B., "New Developments in Particle–Based Immunoassays: Introduction", Pure & Appl. Chem., vol. 68, No. 10, pp. 1873–1879, 1996.
Bangs, L.B., "Latex Immunoassays", J. of Clinical Immunoassay, vol. 13, No. 3, Fall 1990, pp. 127–131.
Hokama, Y., et al., "A Radioimmunoassay for the Detection of Ciguatoxin", Toxicon, vol. 15, pp. 317–325, 1977.
Hokama, Y., "A Rapid, Simplified Enzyme Immunoassay Stick Test for the Detection of Ciguatoxin and Related Polyethers from Fish Tissues", Toxicon, vol. 23, No. 6, pp. 939–946, 1985.
Hokama, Y., et al., "A Rapid Enzyme–Immunoassay for the Detection of Ciguatoxin in Contaminated Fish Tissues", Toxicon, vol. 21, No. 6, pp. 817–824, 1983.

(List continued on next page.)

Primary Examiner—Lynette R. F. Smith
Assistant Examiner—J. Hines
(74) Attorney, Agent, or Firm—James Creighton Wray; Meera P. Narasimhan

(57) ABSTRACT

An immunological test kit suitable for the rapid detection of ciguatoxin and related low molecular weight lipid polyether marine toxins in fish tissues in the field, home or laboratory. The test procedure utilizes a synthetic membrane laminated onto one end of a solid plastic stick, which is immersed into alcohol with a piece of fish tissue. The membrane is then removed and dried thoroughly, then placed in the suspension of mixed colored beads coated with anti-ciguatoxin. The membrane is then rinsed in water and the intensity of the color compared with a standard range of colors formed (0–3+). The color intensity is proportional to the concentration of toxin in the piece of tissue. The kit includes the synthetic membrane on a plastic stick, a suspension of mixed colored beads coated with anti-ciguatoxin antibody, testing instruments, and a supply of solvent.

27 Claims, 2 Drawing Sheets

OTHER PUBLICATIONS

Hokama, Y., "Simplified Solid–Phase Immunobead Assay for Detection of Ciguatoxin and Related Polyethers", J. of Clinical Lab. Analysis, vol. 4, pp. 213–217, 1990.

Hokama, Y., et al., "Monoclonal Antibodies to Ciguatoxin and Related Polyethers", Lecture Notes on Coastal and Estuarine Studies, vol. 25, pp. 155–165, 1988.

Hokama, Y., "Recent Methods for Detection of Seafood Toxins: Recent Immunological Methods for Ciguatoxin and Related Polyethers", Food Additives and Contaminants, vol. 10, No. 1, pp. 71–82, 1993.

Hokama, Y., et al., "Human Intoxications from Hawaiian Reef Fishes Associated with Diverse Marine Toxins", J. of Natural Toxins, vol. 5, pp. 235–247, 1996.

McHugh, T.M., et al., "Development of a Microsphere–Based Fluorescent Immunoassay and its Comparison to an Enzyme Immunoassay for the Detection of Antibodies to Three Antigen Preparations from Candida Albicans", J. Immunological Methods, vol. 116, pp. 213–219, 1989.

* cited by examiner

Negative +/- or weak postive    Strong positive (2-3+)

FIG. 6A   FIG. 6B

= Colored immunobead with anti-ciguatoxin

▷ = Ciguatoxin (epitope)

MEMBRANE IMMUNOBEAD ASSAY FOR THE DETECTION OF CIGUATOXIN AND RELATED POLYETHER MARINE TOXINS

BACKGROUND OF THE INVENTION

The use of latex coated with an antibody for detection of antigens has been known in the clinical art, and especially in the area of visible agglutinative reactions. The procedure is sufficiently specific and sensitive for accurate qualitative and quantitative determinations.

The art has recognized radioimmunoassay, agglutination, and enzyme immunoassay, in both direct and competitive binding assays. In the area of latex immunoassay, colored latex beads having specific antibodies bound to their surface, either chemically or by absorption, are used as a tag for antibodies. The so-called dipstick enzyme, or chemical immunoassay test, is used for rapidly qualitative and semi-quantitative information regarding the presence of analytes.

There has long been a need for a rapid and simple-to-perform procedure for distinguishing edible from potentially toxic fish; in particular, a procedure for detection of ciguatoxins and related low molecular weight polyether marine toxins in fish indigenous to regions where the ecological microflora which cause ciguatera are found. The major source of ciguatoxin is *Gambierdiscus toxicus* (*G. toxicus*) discovered in 1977 at Gambier Island, French Polynesia.

Ciguatoxin has been determined to be the major cause of ciguatera fish poisoning in the tropical and subtropical regions of the world. Ciguatoxin is a marine polyether that is synthesized by *G. toxicus* and then proceeds up the food chain through herbivorous fish and carnivorous fish (e.g., amberjacks, jacks, snappers, groupers, moray eels and barracuda). Ciguatoxin-4B (CTX-4B) from *G. toxicus* is converted to ciguatoxin-1 (CTX-1) in the moray eel liver.

Because more than 24 ciguatoxins (congeners) have been reported, it is unknown whether all species of carnivorous fish associated with ciguatera convert CTX-4B to CTX-1. Thus, a test procedure for analyzing suspect fish flesh should be capable of assessing all congeners and related polyethers of ciguataxin, such as maitotoxin, okadaic acid, brevetoxin and palytoxin, although the toxicity of the congeners may vary. These toxins, particularly ciguatoxin and its related polyether congeners, are able to maintain resinous and fatty substances in water suspension that are highly irritating in their pure form to the skin or mucous membrane.

If ciguatoxin is present in fish tissue or mucous membrane and consumed by humans, it can cause severe ciguatera food poisoning. Such poisoning may cause gastrointestinal, neurological and cardiovascular disorders, and a number of general symptoms. Possible gastrointestinal disorders are vomiting, nausea, stomach pains and diarrhea. Neurological symptoms may include paresthesia and dysesthesia. Cardiovascular effects include bradycardia and tachycardia. General symptoms include taste and vision alteration, itching, and weakness. The most severe general symptoms are muscle aches and joint pains, which may persist for months.

SUMMARY OF THE INVENTION

The present invention is directed to the field of analytical and immunological testimony, and more particularly, to an apparatus and method for testing organic extracts of organisms, vertebrate and invertebrate tissues, marine alga and microorganisms, using synthetic membranes in conjunction with antibody bonding assays and antigen-antibody reaction, especially with lipid epitopes. The reaction utilizes a solid-phase synthetic membrane in which extracted lipid fish toxins bind, and are then detected by antibodies coated onto colored latex beads giving the membrane the color of the beads. The unbound beads (coated with antibody) are then removed by washing in an aqueous solution.

The present invention has been made in view of the above-described inadequacies of the related art and provides a method for detecting ciguatoxin, its congeners and related polyether toxins in fish tissue prior to human consumption.

The present invention provides a method that is simple to perform and provides test results in a short period of time so that the method may be used on location by individuals to sort edible from potentially toxic fish.

The present invention also provides a field test kit for performing the method in accordance with the invention.

A preferred method for detection of ciguatoxin, its congeners and related polyether marine toxins in fish tissue comprises providing a support having a front face and a bottom face. The fish tissue is tested by immersing it into the solvent with the support. The support is removed after soaking with tissue in the solvent for a specified amount of time. The support is tested after it is removed and thoroughly dried. It is then immersed into the immunobead suspension containing mixed colored beads of two different diameters that are coated with anti-ciguatoxin, which is capable of recognizing ciguatoxin and related polyether marine toxins.

The results of the organic extract testing are analyzed by measuring the intensity of the color reaction in the support against a standard control of positive and negative tests.

These and further and other objects and features of the invention are apparent in the disclosure, which includes the above and ongoing written specification, with the claims and the drawings.

BRIEF DESCRIPTION OF THE DRAWINGS

FIG. 1 is a perspective view of the support and membrane structure.

FIG. 2 is a front elevation of the elution of a sample of fish tissue in the solvent to form an extract, which binds to the polyvinylidene fluoride (PVDF) membrane support.

FIG. 3 is a front elevation of the removal of the membrane support for air drying.

FIG. 4 is a front elevation of the immersion of the dried support extract into the suspension of mixed colored beads.

FIG. 5 is a front elevation of the range of color intensities of the membrane after it is removed from immunobead suspension, rinsed in water and dried.

FIGS. 6a and 6b are a schematic of the reaction between the membrane and the immunobead suspension.

DETAILED DESCRIPTION OF THE PREFERRED EMBODIMENT

Figure 7:
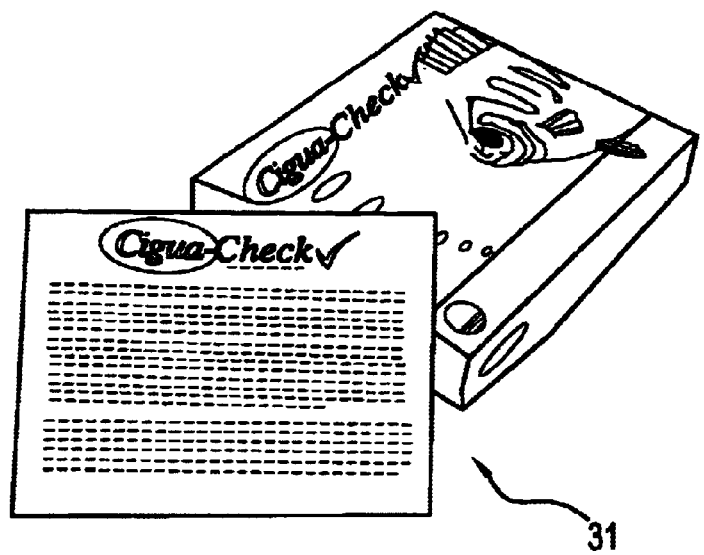
FIG. 7 is a perspective view of the outside of the Cigua-Check Fish Poison Test Kit, showing the instructions.

The invention is a method for testing suspected fish tissue for the detection of the presence of ciguatoxin 25 (shown in FIG. 6), its congeners and related low molecular weight polyether marine toxins, such as maitotoxin, okadaic acid, brevetoxin and palytoxin, and a kit for performing the method. The method is simple to perform, yields rapid results and requires a minimum number of reagents and other testing materials. The method is suitable for field, home, and laboratory use.

Latex beads 15 of two different colors and diameters are coated with anti-ciguatoxin (antibody) 21 in a buffered saline suspension, as shown in FIG. 6. The antibody 21 is directed to recognizing ciguatoxin 25 and related polyether marine toxins. The antibody 21 may be polyclonal or monoclonal and may be produced by a conventional technique. Preferably, the suspension is a phosphate-buffered saline suspension of the beads. Preferred ranges may be between 0.15% to 1.00%, with the anti-ciguatoxin antibody being at a preferred concentration of about 0.5 mg/ml of the suspension. In preferred embodiments, the solution may include between 60 in amounts of about 0.5% and about 0.05% sodium azide.

Referring to FIG. 2, a fish is tested by removing a piece of sample 11 using a sharp tool (razor blade or sharp knife) and placing the piece of tissue in a volume of solvent 9, together with a membrane 5 and element or support 3. The membrane 5 and element or support 3 is removed after soaking for a specific time and is thoroughly air dried.

The dried membrane 5 with the lipids from the fish is then immersed into a specific aqueous volume in a separate vial 23 containing the latex beads 15 of two different colors and sizes coated with the anti-ciguatoxin 21, as shown in FIGS. 6a and 6b. The membrane 5 and support 3 are immersed for a specific time. The membrane 5 is then removed, washed, and dried.

The method uses known test conditions to ensure consistent results. Semi-quantitative test information is obtained by comparing the intensity of the color on the membrane 5 by referring to a standard data (colored chart 27 of FIG. 8b) obtained from known concentrations of ciguatoxin.

The testing procedure comprises initially removing a piece of tissue 11 from a fish using a conventional cutting tool, such as a knife. The fish tissue 11 is preferably removed in the form of a cube having approximately 0.5 inch sides.

The fish tissue 11 is next cut into one or more smaller samples 11 of a suitable size for subsequent testing. Using a razor or knife, the large fish sample is cut into cube sizes of approximately 2 mm sides. Such samples 11 weigh approximately 5.0 ±10mg based on the density of the fish tissue. FIGS. 2 3 and 4 illustrate the manner of performing a field Cigua-Check test for detection of ciguatoxins 25, its congeners, and its related polyether toxins in prepared fish samples.

FIG. 1 is a schematic of a support 3 preferably composed of a solid plastic material, on which a polyvinylidene (PVDF) hydrophobic membrane 5 having a pore size of 0.45μm is adhered. The membrane 5 may be adhered by a suitable adhesive such as double-sided tape or the like. The support 3 preferably has a height of about 80 mm, a width of about 7.0 mm and a thickness of about 1 mm. The membrane 5 preferably covers a certain portion of the front face of the support. The membrane 5 has a height of about 20 mm and covers one end of the support.

The anti-ciguatoxin (protein in a mixture) 21, preferably added to two groups of colored beads 15 of diameters of 0.318 μm (blue) and 0.124 μm(red) in 0.1% bead suspension in saline 13. The bead suspension is placed in a vial 23 separate from the organic solvent 9, as shown in FIGS. 6a and 6b.

As depicted in FIG. 2, a fish tissue sample 11 is immersed together with the membrane 5 and support 3 in about 0.5 ml of a solvent 9 contained in a vial 7, or a like container having an open end. The solvent 9 is preferably absolute methyl alcohol. For a single test, a vial 7 with 0.5 ml supply of the methanol is provided in the Cigua-Check kit 31.

In another preferred embodiment, for the testing of a plurality of fish tissue samples 11, a plurality of supports 3 and a separate closed vial 7 containing approximately 0.5 ml of methanol for each membrane 5 and support 3 are provided.

For each test, the fish tissue 11 is immersed, together with the membrane 5 and support 3, in the solvent 9 for a sufficient amount of time for the fish lipids to bind to the membrane 5. The preferred period is about twenty minutes.

After the fish tissue FIG. 2 and the membrane 5 have been immersed in the vial for a sufficient amount of time, the membrane 5 and support 3 are then removed and thoroughly air dried for approximately fifteen minutes (or longer). The dried membrane 5 (see FIG. 3) is immersed into the immunobead suspension 13 in vial 23, as shown in FIG. 4, for approximately ten minutes. The membrane 5 and support 3 are then removed from the immunobead suspension 13, rinsed with water and dried by blotting with tissue paper. The color intensity of the membranes 5 are read and compared with the controls, as shown in FIG. 5. A membrane 5 showing no color 6 indicates a negative test result. A membrane 5 showing light coloring 8 indicates a weak positive. A membrane 5 showing strong coloring 10 indicates a strong positive. The unknown sample 11 tested in a similar manner in parallel with the controls is compared with the controls and a standard color chart 27, shown in FIG. 8b reading from 0–3+. Any color of 1+, or greater, indicates a higher risk for toxicity, and the fish from which the sample was taken should be considered non-edible.

FIGS. 6a and 6b show a schematic of the reaction between the membrane 5 and the immunobead suspension 13. The membrane 5 is adhered to the support 3, and is immersed in the fish tissue extract where ciguatoxin 25 adheres to the membrane 5. When the membrane 5 is dried and immersed in the immunobead suspension 13, the attraction between the ciguatoxin 25 on the membrane and the anti-ciguatoxin antibodies 21 causes the beads 15 to become attached to the membrane 5.

Figure 8A:
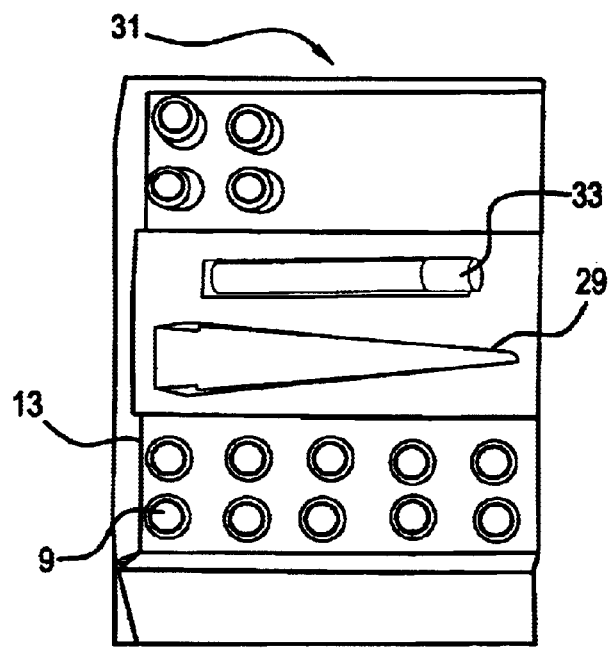
FIGS. 8a and 8b are a perspective view of the interior of the Cigua-Check Fish Poison Test Kit, showing forceps, membrane supports in tube, row of solvent and row of immunobead suspensions. A
Figure 8B:
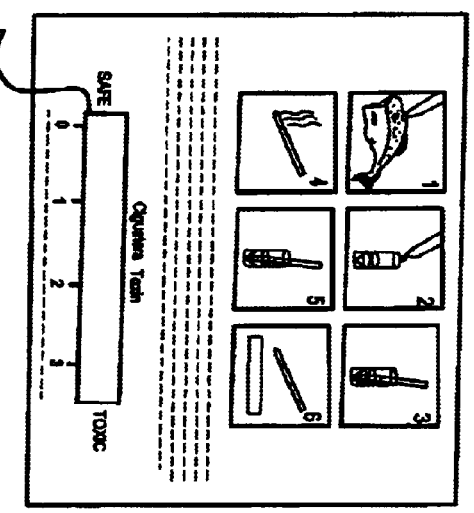

FIGS. 7 and 8a,b show outer and inner perspective views of the Cigua-Check Test Kit 31, which has been developed for commercialization purposes. FIG. 7 is the complete Cigua-Check Test Kit with information on ciguatera poisoning and a listing of the general contents of the kit on the outside. FIG. 8a is the inside of the box showing the arrangements and contents including solvents 9, immunobead suspension 13, forceps 29, and a tube 33 containing the membranes 5 and supports 3.

While the invention has been described with reference to specific embodiments, modifications and variations of the invention may be constructed without departing from the scope of the invention, which is defined in the following claims.

We claim:

1. A portable kit for in situ detection of toxins in fish tissue comprising a first container, a solvent in the first container for extracting toxins from fish tissue and for facilitating toxin binding to the membrane, a second container, a solution in the second container, a suspension of plural detectors in the solution for detecting the toxins, at least one support element, a membrane on a portion of the at least one support element, and a data standard for comparing data indicated by the membrane and determining ciguatoxin concentration.

2. The kit of claim 1, wherein the detected toxins are ciguatoxins.

3. The kit of claim 1, wherein the detected toxins are polyether marine toxins.

4. The kit of claim 1, wherein the membrane is a porous membrane.

5. The kit of claim 1, wherein the solvent is an organic solvent.

6. The kit of claim 1, wherein the solution is a saline solution.

7. The kit of claim 1, further comprising a third container for holding the at least one support element and the membrane.

8. The kit of claim 1, wherein the support element further comprises first and second ends, and wherein the membrane covers a portion of the first end of an outer surface and the remaining portion of an outer surface is uncovered.

9. The kit of claim 1, wherein the membrane is composed of polyvinylidene fluoride (PVDF).

10. The kit of claim 1, wherein the membrane has a pore size of 0.45 $\mu$m.

11. The kit of claim 1, wherein the solvent is methanol.

12. The kit of claim 1, wherein the detectors are latex beads.

13. The kit of claim 11, wherein the latex beads are coated with an anti-ciguatoxin antibody.

14. The kit of claim 12, wherein the solution is a 1.0% phosphate-buffered saline suspension of the beads, and wherein the anti-ciguatoxin antibody is at a concentration of about 0.5 mg (protein)/ml of the suspension.

15. The kit of claim 12, wherein the solution is a 0.85% phosphate-buffered saline suspension of the beads, and wherein the anti-ciguatoxin antibody is at a concentration of about 0.5 mg (protein)/ml of the suspension.

16. The kit of claim 12, wherein the solution is a 0.15% phosphate-buffered saline suspension of the beads, and wherein the anti-ciguatoxin antibody is at a concentration of about 0.5 mg (protein)/ml of the suspension.

17. The kit of claim 1, further comprising comparing detectors on the support element with a data standard representing known ciguatoxin concentrations for comparing detectors on the support element with the data standard for estimating ciguatoxin concentration in fish tissues.

18. The kit of claim 15, wherein the data standard is a color standard chart.

19. The kit of claim 15, wherein the data standard is a collection of control samples with known concentrations of ciguatoxin.

20. The kit of claim 15, further comprising a spectrometer for comparing the color intensity of the fish tissues with standard data.

21. The kit of claim 1, further comprising forceps for handling fish tissues.

22. The kit of claim 1, further comprising a knife for preparing fish tissues.

23. The kit of claim 1, further comprising a razor for preparing fish tissues.

24. The kit of claim 1, further comprising a housing for receiving the kit.

25. The kit of claim 1, wherein the fish tissue weighs about 5.0 mg.

26. The kit of claim 1, wherein the solvent measures about 0.5 ml.

27. The kit of claim 1, wherein the solution comprises about 0.5% Tween 60 and 0.05% sodium azide.

* * * * *